US010791827B2

(12) United States Patent
Hoffman et al.

(10) Patent No.: US 10,791,827 B2
(45) Date of Patent: Oct. 6, 2020

(54) PHARMACY ORDER PROCESSING SYSTEM

(71) Applicant: Express Scripts Strategic Development, Inc., St. Louis, MO (US)

(72) Inventors: Robert E. Hoffman, Linden, IN (US); Steven R. Hinkle, Olive Branch, MS (US); Jarrod A. Killough, Mesa, AZ (US)

(73) Assignee: Express Scripts Strategic Development, Inc., St. Louis, MO (US)

( * ) Notice: Subject to any disclaimer, the term of this patent is extended or adjusted under 35 U.S.C. 154(b) by 0 days.

(21) Appl. No.: 16/556,671

(22) Filed: Aug. 30, 2019

(65) Prior Publication Data

US 2019/0385724 A1 Dec. 19, 2019

Related U.S. Application Data

(62) Division of application No. 15/863,801, filed on Jan. 5, 2018, now Pat. No. 10,424,408.

(51) Int. Cl.
*A47B 21/02* (2006.01)
*A47B 9/00* (2006.01)

(52) U.S. Cl.
CPC ................ *A47B 21/02* (2013.01); *A47B 9/00* (2013.01); *A47B 2200/0056* (2013.01);
(Continued)

(58) Field of Classification Search
CPC ............ A47B 21/02; A47B 2200/0061; A47B 2200/0066; A47B 2200/0056
See application file for complete search history.

(56) References Cited

U.S. PATENT DOCUMENTS 5,771,657 A 6/1998 Lasher et al.
7,185,477 B2 3/2007 Rice et al.
(Continued)

FOREIGN PATENT DOCUMENTS

CA 2833710 11/2017
WO 2017076595 5/2017

OTHER PUBLICATIONS

International Search Report and the Written Opinion of the International Searching Authority in International Applicatio No. PCT/US2018/066134 (17 pages), May 14, 2019.

*Primary Examiner* — Thomas Randazzo
(74) *Attorney, Agent, or Firm* — Dickinson Wright PLLC

(57) ABSTRACT

In one aspect, a pharmacy order processing system is disclosed. The system includes a plurality of picking workstations, each picking workstation including a plurality of bins. The system also includes a plurality of trays for carrying a plurality of pharmacy orders, a tray drop-off station, and a tray delivery conveyor extending between the tray drop-off station and the plurality of picking workstations. The system further includes a tray delivery conveyor extending between the tray drop-off station and the plurality of picking workstations. The system includes a plurality of packing workstations, each packing workstation including an opening to receive a scale and a plurality of receptacles configured to receive shipping label printers. The system also includes at least one inspection workstation, the at least one inspection workstation including at least one product scanner. The system further includes a packing delivery conveyor extending from the plurality of packing workstations.

17 Claims, 11 Drawing Sheets

(52) U.S. Cl.
CPC ............... *A47B 2200/0061* (2013.01); *A47B 2200/0066* (2013.01); *B65G 2201/0258* (2013.01); *B65G 2201/0261* (2013.01)

(56) References Cited

U.S. PATENT DOCUMENTS

| | | | |
|---|---|---|---|
| 7,748,628 | B2 | 7/2010 | Greyshock |
| 7,765,776 | B1 | 8/2010 | Leu et al. |
| 8,333,053 | B2 | 12/2012 | Mahar |
| 8,600,903 | B2 | 12/2013 | Eller |
| 8,713,897 | B2 | 5/2014 | Luciano, Jr. et al. |
| 9,174,758 | B1 | 11/2015 | Rowley et al. |
| 9,242,751 | B1 | 1/2016 | Joplin et al. |
| 9,394,107 | B1 | 7/2016 | Eller et al. |
| 9,567,119 | B2 | 2/2017 | Joplin |
| 9,697,335 | B2 | 7/2017 | Joplin |
| 9,868,558 | B2 | 1/2018 | Holmes |
| 2005/0125097 | A1 | 6/2005 | Chudy et al. |
| 2007/0150383 | A1 | 6/2007 | Shakes |
| 2010/0089997 | A1 | 4/2010 | Carson |
| 2011/0146835 | A1 | 6/2011 | Terzini |
| 2012/0073241 | A1 | 3/2012 | Mahar |
| 2013/0151005 | A1 | 6/2013 | Gerold et al. |
| 2013/0248547 | A1 | 9/2013 | Braun et al. |
| 2013/0310969 | A1 | 11/2013 | Terzini et al. |
| 2014/0025545 | A1 | 1/2014 | Carson et al. |
| 2014/0208986 | A1* | 7/2014 | DesRoches ............ G05B 15/02 108/22 |
| 2016/0023790 | A1 | 1/2016 | Joplin et al. |
| 2016/0026774 | A1 | 1/2016 | Joplin |
| 2017/0107005 | A1 | 4/2017 | Joplin |
| 2017/0308675 | A1 | 10/2017 | Parviainen |
| 2018/0103753 | A1* | 4/2018 | Davidsen ................ A47B 9/20 |
| 2018/0186572 | A1 | 7/2018 | Issing |
| 2018/0235360 | A1* | 8/2018 | Li ........................ A47B 21/06 |
| 2018/0279770 | A1* | 10/2018 | Crowe ................... A47B 9/10 |
| 2019/0059574 | A1* | 2/2019 | Paul ....................... A47B 9/02 |
| 2019/0223586 | A1* | 7/2019 | Hansen .................. A47B 9/00 |

* cited by examiner

PHARMACY ORDER PROCESSING SYSTEM

CROSS REFERENCE TO RELATED APPLICATIONS

This application is a divisional application of U.S. patent application Ser. No. 15/863,801, filed on Jan. 5, 2018. The entire disclosure of the application referenced above is incorporated by reference.

FIELD

The present disclosure relates generally to the technical field of pharmacy order processing, and more particularly, to methods and systems for processing custom pharmacy orders, especially in a high volume, specialty, or partially-automated order processing center.

BACKGROUND

This Background section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

Pharmaceutical order processing systems typically involve labor intensive processes to retrieve, fill, and package the many pharmacy orders. Many of the pharmacy orders are custom or specialty orders that are currently filled manually, and thus the process for filling the orders is difficult to fully automate or standardize. Improved systems and methods for filling custom or specialty pharmacy orders at a high volume to improve order fulfillment realization and customer satisfaction are needed.

BRIEF SUMMARY

In one aspect, a pharmacy order processing system comprises a plurality of picking workstations, each picking workstation including a plurality of bins, a plurality of trays for carrying a plurality of pharmacy orders, a tray drop-off station and a tray delivery conveyor extending between the tray drop-off station and the plurality of picking workstations. The processing system further comprises a plurality of packing workstations, each packing workstation including an opening to receive a scale and a plurality of receptacles configured to receive shipping label printers. The system also comprises at least one inspection workstation, the at least one inspection workstation including at least one product scanner, and a packing delivery conveyor extending from the plurality of packing workstations.

In another aspect, a workstation for a pharmacy order processing system comprises a support frame, a desktop connected to the support frame, and an accessory frame connected to a rear portion of the support frame. The support frame includes storage bins connected to the accessory frame and a base connected to the support frame. The base includes four legs, each leg including an outer sleeve, an inner support positioned within the outer sleeve, and an extension motor positioned within each leg and configured to extend the inner support relative to the outer sleeve.

In yet another aspect, a method of filling a prescription order includes receiving a prescription order request at a picking workstation, wherein the prescription order request includes prescription preparation information. The method also includes placing a plurality of retrieved products on a tray to form a filled order and placing the tray containing the filled order on a filled order delivery conveyor, the filled order delivery conveyor extending between the picking workstation and a packing workstation. The method further includes inspecting, at an inspection workstation, the filled order, and receiving, at a packing workstation, the tray containing the filled order. The method includes generating and affixing product labels to the retrieved products of the filled order at the packing workstation. Finally, the method includes placing a container containing the packed order on a packed order delivery conveyor, wherein the packed order delivery conveyor extends between the packing workstation and a shipping conveyor.

Various refinements exist of the features noted in relation to the above-mentioned aspects. Further features may also be incorporated in the above-mentioned aspects as well. These refinements and additional features may exist individually or in any combination. For instance, various features discussed below in relation to any of the illustrated embodiments may be incorporated into any of the above-described aspects, alone or in any combination.

BRIEF DESCRIPTION OF THE DRAWINGS

In the drawings, reference numbers may be reused to identify similar and/or identical elements.

DETAILED DESCRIPTION

Example systems and methods for processing a pharmacy order, for example, in a pharmacy, are described. In the following description, for purposes of explanation, numerous specific details are set forth in order to provide a thorough understanding of example embodiments. It will be evident, however, to one of ordinary skill in the art that these embodiments may be practiced without these specific details.

Generally, a prescription order is generated for a pharmacy, and in some embodiments a high volume pharmacy. The prescription order may include more than one prescription drug for fulfillment. Each prescription drug in a prescription order is an order component of the prescription order. Generally, the order components are pill bottles, liquid bottles, blister packs, unit-of-use packs, injectable package, spray bottles, tubes, ampoules, drop counters, insulated boxes, child-resistant containers, or other packaging having a quantity of a prescription drug contained therein.

Figure 1:
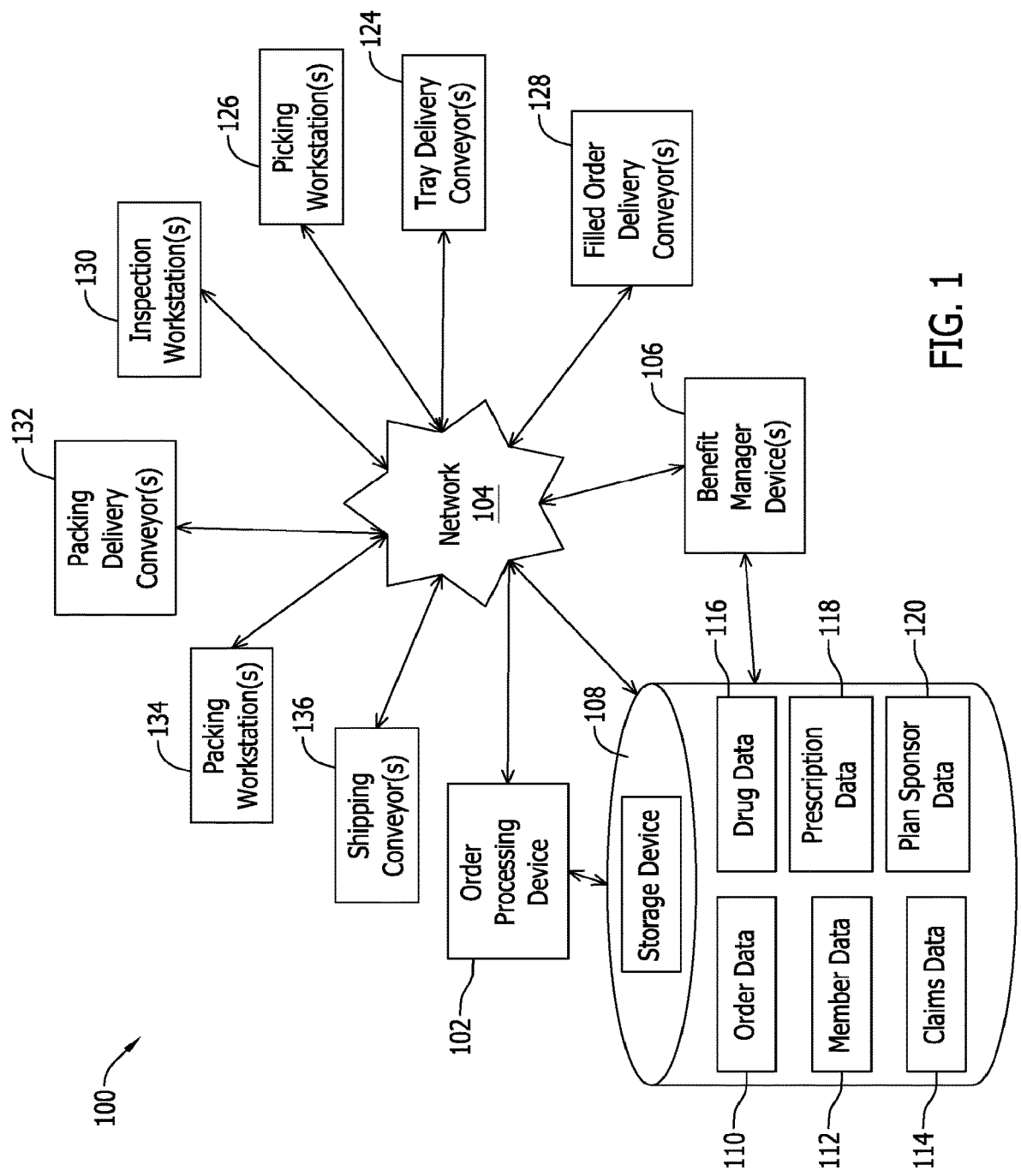
FIG. 1 is a block diagram of an example implementation of a pharmacy order processing system, according to an example embodiment.

FIG. 1 is a block diagram of an example implementation of a prescription order processing system 100 for a specialty pharmacy, according to an example embodiment. While the prescription order processing system 100 is generally described as being deployed in a specialty or a fulfillment center (e.g., a mail order pharmacy, a direct delivery pharmacy, etc., and the like), the prescription order processing system 100 and/or components thereof may otherwise be deployed (e.g., in a high volume pharmacy, etc.). A specialty pharmacy may be a pharmacy that is capable of filling prescriptions automatically, mechanically, manually, or a combination thereof. The prescription order processing system 100 may include a benefit manager device 106 and an order processing device 102 in communication with each other directly and/or over a network 104. The system may also include a storage device 108.

The benefit manager device 106 is a device operated by an entity that is at least partially responsible for creation and/or management of the pharmacy or drug benefit. While such entity operating the benefit manager device 106 is typically a pharmacy benefit manager (PBM), other entities may operate the benefit manager device 106 on behalf of themselves (i.e., the PBMs) or other entities. For example, the benefit manager device 106 may be operated by a health plan, a retail pharmacy chain, a drug wholesaler, a data analytics, or other type of software-related company, etc., or the like. In some embodiments, a PBM that provides the pharmacy benefit may also provide one or more than one additional benefits including a medical or health benefit, a dental benefit, a vision benefit, a wellness benefit, a radiology benefit, a pet care benefit, an insurance benefit, a long term care benefit, a nursing home benefit, etc., and the like. The PBM may, in addition to its PBM operations, operate one or more than one pharmacies. The pharmacies may be retail pharmacies, mail order pharmacies, etc.

Some of the operations of the PBM that operates the benefit manager device 106 may include the following activities and processes. A member (or a person on behalf of the member) of a pharmacy benefit plan may obtain a prescription drug at a retail pharmacy location (e.g., a location of a physical store, etc.) from a pharmacist or a pharmacist technician. The member may also obtain the prescription drug through mail order drug delivery from a mail order pharmacy location, which may be the prescription order processing system 100. In some embodiments, the member may obtain the prescription drug directly or indirectly through the use of a machine, such as a kiosk, vending unit, mobile electronic device, or a different type of mechanical, electrical, electronic communication device and/or computing device. Such a machine may be filled with the prescription drug in prescription packaging, which may include multiple prescription components, by the prescription order processing system 100. The pharmacy benefit plan is administered by or through the benefit manager device 106.

The member may have a copayment for the prescription drug that reflects an amount of money that the member is responsible to pay the pharmacy for the prescription drug. The money paid by the member to the pharmacy may come from personal funds of the member, a health savings account (HSA) of the member or the member's family, a health reimbursement arrangement (HRA) of the member or the member's family, a flexible spending account (FSA) of the member or the member's family, etc., or the like. In some instances, an employer of the member may directly or indirectly fund or reimburse the member for the copayments.

The amount of the copayment required by the member may vary with different pharmacy benefit plans having different plan sponsors or clients and/or for different prescription drugs. The member's copayment may be a flat copayment (e.g., $10, etc.), co-insurance (e.g., 10%, etc.), and/or a deductible (e.g., for first $500 of annual prescription drug expense, etc.) for certain prescription drugs, certain types and/or classes of prescription drugs, and/or all prescription drugs. The copayment may be stored in the storage device 108 or determined by the benefit manager device 106.

In some instances, the member may not pay the copayment or may only pay a portion of the copayment for the prescription drug. For example, if a usual and customary cost for a generic version of a prescription drug is $4, and the member's flat copayment is $20 for the prescription drug, the member may only need to pay $4 to receive the prescription drug. In another example involving a worker's compensation claim, no copayment may be due by the member for the prescription drug.

In addition, copayments may also vary based on different delivery channels used for the prescription drug to be received. For example, the copayment for receiving the prescription drug from a mail order pharmacy location may be less than the copayment for receiving the prescription drug from a retail pharmacy location.

In conjunction with receiving a copayment (if any) from the member and dispensing the prescription drug to the member, the pharmacy submits a claim to the PBM for the prescription drug. After receiving the claim, the PBM, e.g., the benefit manager device, may perform certain adjudication operations including verifying eligibility for the member, identifying/reviewing an applicable formulary for the member to determine any appropriate copayment, coinsurance, and deductible for the prescription drug, and performing a drug utilization review (DUR) on the member. Further, the PBM may provide a response to the pharmacy, e.g., the pharmacy prescription order processing system 100, following performance of at least some of the aforementioned operations.

As part of the adjudication, a plan sponsor (or the PBM on behalf of the plan sponsor) ultimately reimburses the pharmacy for filling the prescription drug when the prescription drug was successfully adjudicated.

The aforementioned adjudication operations generally occur before the copayment is received and the prescription drug is dispensed. However in some instances, these operations may occur simultaneously, substantially simultaneously, or in a different order. In addition, more or less adjudication operations may be performed as at least part of the adjudication process.

The amount of reimbursement paid to the pharmacy by a plan sponsor and/or money paid by the member may be determined at least partially based on types of pharmacy network in which the pharmacy is included. In some embodiments, the amount may also be determined based on other factors. For example, if the member pays the pharmacy for the prescription drug without using the prescription or drug benefit provided by the PBM, the amount of money paid by the member may be higher than when the member uses the prescription or drug benefit. In some embodiments, the amount of money received by the pharmacy for dispensing the prescription drug and for the prescription drug itself may be higher than when the member uses the prescription or drug benefit. Some or all of the foregoing operations may be performed by executing instructions stored in the benefit manager device 106 and/or an additional device.

Examples of the network 104 include Mobile Communications (GSM) network, a code division multiple access (CDMA) network, 3rd Generation Partnership Project (3GPP), an Internet Protocol (IP) network, a Wireless Application Protocol (WAP) network, a WiFi network, or an IEEE 802.11 standards network, as well as various combinations thereof. The network 104 may include optical network. The network 104 may be a local area network or a global communication network, such as the Internet. In some embodiments, the network 104 may include a network dedicated to prescription orders, e.g., a prescribing network such as the electronic prescribing network operated by Surescripts of Arlington, Va.

Moreover, although the system shows a single network 104, multiple networks can be used. The multiple networks may communicate in series with each other to link the devices 102-110 or in parallel to link the devices 102-110.

The order processing device 102 may be a device associated with a retail pharmacy location (e.g., an exclusive pharmacy location, a grocery store with a retail pharmacy, or a general sales store with a retail pharmacy) or other type of pharmacy location at which a member attempts to obtain a prescription. The order processing device 102 may be utilized by the pharmacy to submit the claim to the PBM for adjudication.

Additionally, in some embodiments, the order processing device 102 may enable information exchange between the pharmacy and the PBM, for example, to allow the sharing of member information such as drug history, and the like, that may allow the pharmacy to better service a member (e.g., by providing more informed therapy consultation and drug interaction information, etc.). In some embodiments, the benefit manager device 106 may track prescription drug fulfillment and/or other information for patients that are not members or have not identified themselves as members, at the time (or in conjunction with the time) in which they seek to have a prescription filled at a pharmacy.

The order processing device 102 may receive information regarding filling prescriptions and may direct an order component to one or more devices of the prescription order processing system 100 at a pharmacy. The order processing device 102 may fulfill, dispense, aggregate, and/or pack the order components of the prescription drugs in accordance with one or more prescription orders directed by the prescription order processing system 100. The order processing device 102 may be deployed in the prescription order processing system 100, or may otherwise be used.

In general, the order processing device 102 is a device located within or otherwise associated with the pharmacy to enable fulfillment of a prescription and dispensing prescription drugs. In some embodiments, the order processing device 102 may be an external device separate from the pharmacy and may communicate with other devices located within the pharmacy.

For example, the external order processing device 102 may communicate with an internal order processing device 102 and/or other devices located within the prescription order processing system 100. In some embodiments, the external order processing device 102 may have limited functionality (e.g., as operated by a patient requesting fulfillment of a prescription drug), while the internal order processing device 102 may have greater functionality (e.g., as operated by a pharmacist).

The order processing device 102 may track the prescription order as it is fulfilled by the prescription order processing system 100. The prescription order may include one or more than one prescription drugs to be filled by the pharmacy. The order processing device 102 may make pharmacy routing decisions and/or order consolidation decisions for the particular prescription order. The pharmacy routing decisions include what device(s) in the pharmacy are responsible for filling or otherwise handling certain portions of the prescription order. The order consolidation decisions include whether portions of one prescription order or multiple prescription orders should be shipped together for a patient or a patient family. The order processing device 102 may also track and/or schedule literature or paperwork associated with each prescription order or multiple prescription orders that are being shipped together.

The order processing device 102 may include circuitry, a processor, a memory to store data and instructions, and communication functionality. The order processing device 102 is dedicated to performing processes, methods and/or instructions described herein. Other types of electronic devices specifically configured to implement with the processes, methods and/or instructions described herein may also be used.

In some embodiments, at least some functionalities of the order processing device 102 may be included in the benefit manager device 106. The order processing device 102 may be in a client-server relationship with the benefit manager device 106, in a peer-to-peer relationship with the benefit manager device 106, or in a different type of relationship with the benefit manager device 106. The order processing device 102 and/or the benefit manager device 106 may communicate directly (e.g., by utilizing a local storage, etc.) and/or through the network 104 (e.g., by utilizing a cloud configuration or software as a service, etc.) with the storage device 108.

The storage device 108 may include: a non-transitory storage (e.g., memory, hard disk, CD-ROM, etc.) in communication with the benefit manager device 106, and/or the order processing device 102 directly and/or over the network 104. The non-transitory storage may store order data 110, member data 112, claims data 114, drug data 116, prescription data 118, and/or plan sponsor data 120. Further, the prescription order processing system 100 may include additional devices, which may communicate with each other directly or over the network 104.

The order data 110 may be related to a prescription order. The order data may include type of the prescription drug (e.g., drug name and strength, etc.) and quantity of the prescription drug, etc. The order data 110 may also include data used for completion of the prescription, such as prescription materials. In general, prescription materials include an electronic copy of information regarding the prescription drug for inclusion with or otherwise in conjunction with the fulfilled prescription. The prescription materials may include electronic information regarding drug interaction warnings, recommended usage, possible side effects, expiration date, date of prescribing, or the like. The order data 110 may be used by a high volume fulfillment center to fulfill a pharmacy order.

In some embodiments, the order data 110 includes verification information associated with fulfillment of the prescription in the pharmacy. For example, the order data 110 may include videos and/or images taken of (i) the prescription drug prior to dispensing, during dispensing, and/or after dispensing, (ii) the prescription container (e.g., a prescription bottle and sealing lid, prescription packaging and the like) used to contain the prescription drug prior to dispensing, during dispensing, and/or after dispensing, (iii) the packaging and/or packaging materials used to ship or otherwise deliver the prescription drug prior to dispensing, during dispensing, and/or after dispensing, and/or (iv) the fulfillment process within the pharmacy. Other type of verification information such as bar code data read from pallets, bins, trays, carts, and the like used to transport prescriptions within the pharmacy may also be stored as order data 110.

The member data 112 includes information regarding the members associated with the PBM. The information stored as member data 112 may include personal information, personal health information, protected health information, and the like. Examples of the member data 112 include name, address, telephone number, e-mail address, prescription drug history, etc., and the like. The member data 112 may include a plan sponsor identifier that identifies the plan sponsor associated with the member and/or a member identifier that identifies the member to the plan sponsor. The member data 112 may include a member identifier that identifies the plan sponsor associated with the patient and/or a patient identifier that identifies the patient to the plan sponsor. The member data 112 may also include, by way of example, dispensation preferences such as type of label, type of cap, message preferences, language preferences, or the like.

The member data 112 may be accessed by various devices in the pharmacy, (e.g., the high volume fulfillment center, etc.), to obtain information utilized for fulfillment and shipping of prescription orders. In some embodiments, an external order processing device 102 operated by or on behalf of a member may have access to at least a portion of the member data 112 for review, verification, etc., or other purposes.

In some embodiments, the member data 112 may include information for persons who are patients of the pharmacy but are not members in the pharmacy benefit plan being provided by the PBM. For example, these patients may obtain drug directly from the pharmacy, through a private label service offered by the pharmacy, the high volume fulfillment center, or otherwise. In general, the use of the terms member and patient may be used interchangeably herein.

The claims data 114 includes information regarding pharmacy claims adjudicated by the PBM under a drug benefit program provided by the PBM for one, or more than one, plan sponsors. In general, the claims data 114 includes an identification of the client that sponsors the drug benefit program under which the claim is made, and/or the member that purchased the prescription drug giving rise to the claim, the prescription drug that was filled by the pharmacy (e.g., the national drug code number, etc.), the dispensing date, generic indicator, GPI number, medication class, the cost of the prescription drug provided under the drug benefit program, the copay/coinsurance amount, rebate information, and/or member eligibility, etc. Additional information may be included.

In some embodiments, other types of claims beyond prescription drug claims may be stored in the claims data 114. For example, medical claims, dental claims, wellness claims, or other type of health care-related claims for members may be stored as a portion of the claims data 114.

In some embodiments, the claims data 114 includes claims that identify the members with whom the claims are associated. In some embodiments, the claims data 114 includes claims that have been de-identified (e.g., associated with a unique identifier but not with a particular, identifiable member, etc.).

The drug data 116 may include drug name (e.g., technical name and/or common name, etc.), other names by which the drug is known by, active ingredients, an image of the drug (e.g., in pill form, etc.), and the like. The drug data 116 may include information associated with a single medication or multiple medications.

The prescription data 118 may include information regarding prescriptions that may be issued by prescribers on behalf of patients, who may be members of the pharmacy benefit plan, for example to be filled by a pharmacy. Examples of the prescription data 118 include patient names, medication or treatment (such as lab tests), dosing information, and the like. The prescriptions may be electronic prescriptions, paper prescriptions that have been scanned, or otherwise. In some embodiments, the dosing information reflects a frequency of use (e.g., once a day, twice a day, before each meal, etc.) and a duration of use (e.g., a few days, a week, a few weeks, a month, etc.).

In some embodiments, the order data 110 may be linked to associated member data 112, claims data 114, drug data 116, and/or prescription data 118.

The plan sponsor data 120 includes information regarding the plan sponsors of the PBM. Examples of the plan sponsor data 120 include company name, company address, contact name, contact telephone number, contact e-mail address, etc., and the like.

Figure 2:
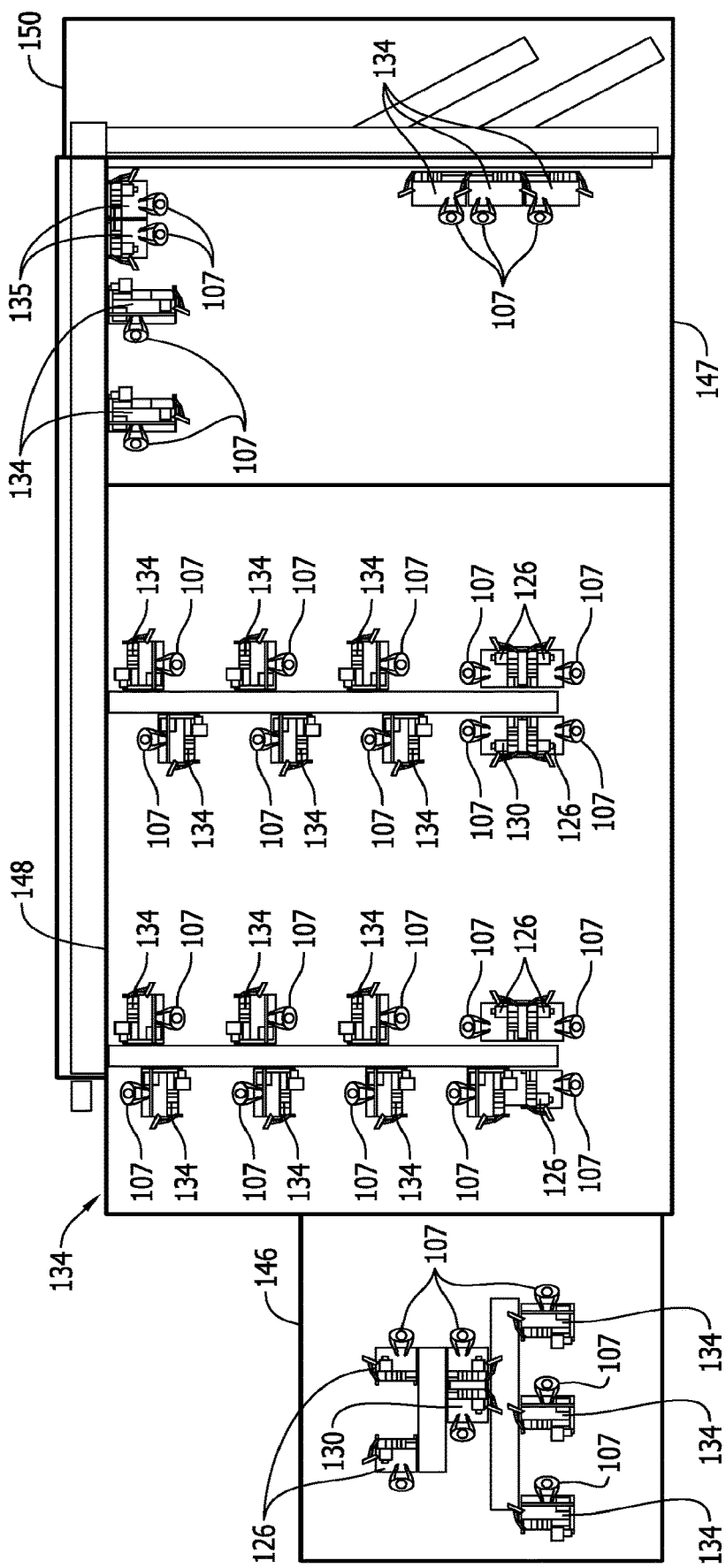
FIG. 2 is a plan view of a layout of the pharmacy order processing system shown in FIG. 1 according to an example embodiment.

FIG. 2 is a plan view of a layout of the prescription order processing system 100. The prescription order processing system 100 is configured to rapidly process, using a plurality of operators 107 at a number of stations, pharmacy orders from receipt of an order to shipping a packed filled order.

In the example embodiment, prescription order processing system 100 includes an ambient conditions section 146, a refrigerated conditions section 148, an ATX section 147, and a shipping section 150. Each of the ambient conditions section 146 and the refrigerated conditions section 148 includes a plurality of picking workstations 126, a plurality of packing workstations 134, and at least one inspection workstation 130, each workstation assigned one operator 107. The ATX section 147 includes two packing workstations 134 and a pair of quality assurance workstations 135. In some embodiments, prescription order processing system 100 may include as many types and number of workstations and operators 107 as facilitates operation of the prescription order processing system 100. As will be understood by one of ordinary skill, the ambient conditions section 146 is maintained at substantially room temperature, and the refrigerated conditions section 148 includes portions that are maintained at a temperature that is less than the ambient temperature. In the example embodiment, refrigerated conditions section 148 includes a plurality of reach-in coolers that maintain internal temperatures of between approximately 36° F. and 46° F., and at least one walk-in freezer that maintains an internal temperature of between approximately −14° F. and 14° F. In the example embodiment, each cooler and freezer includes a temperature alarm that sounds if a given temperature range is not met within a respective cooler or freezer for a 15 minute period.

In this embodiment, prescription order processing system 100 includes a plurality of ambient conveyors 137 and a plurality of conveyor assemblies 138. The ambient section 146 includes two ambient conveyors 137. One ambient conveyor 137 extends between the ambient picking workstations 126 and is positioned adjacent to the ambient inspection workstation 130. The second ambient conveyor 137 extends between the ambient packing workstations 134 and is positioned adjacent to the ambient inspection workstation 130 opposite to the first ambient conveyor 137. The refrigerated section 148 includes two conveyor assemblies 138 and a shipping conveyor 136. The first of the conveyor assemblies 138 extends from a first group of refrigerated picking workstations 126 through a first group refrigerated packing workstations 134 to an intersection with the shipping conveyor 136. The second of the conveyor assemblies 138 extends from a second group of refrigerated picking workstations 126, past a refrigerated inspection workstation 130, and through a second group of refrigerated packing workstations 134 to an intersection with the shipping conveyor 136. The shipping conveyor 136 extends from intersections with each of the conveyor assemblies 138 to the shipping section 150.

Figure 3:
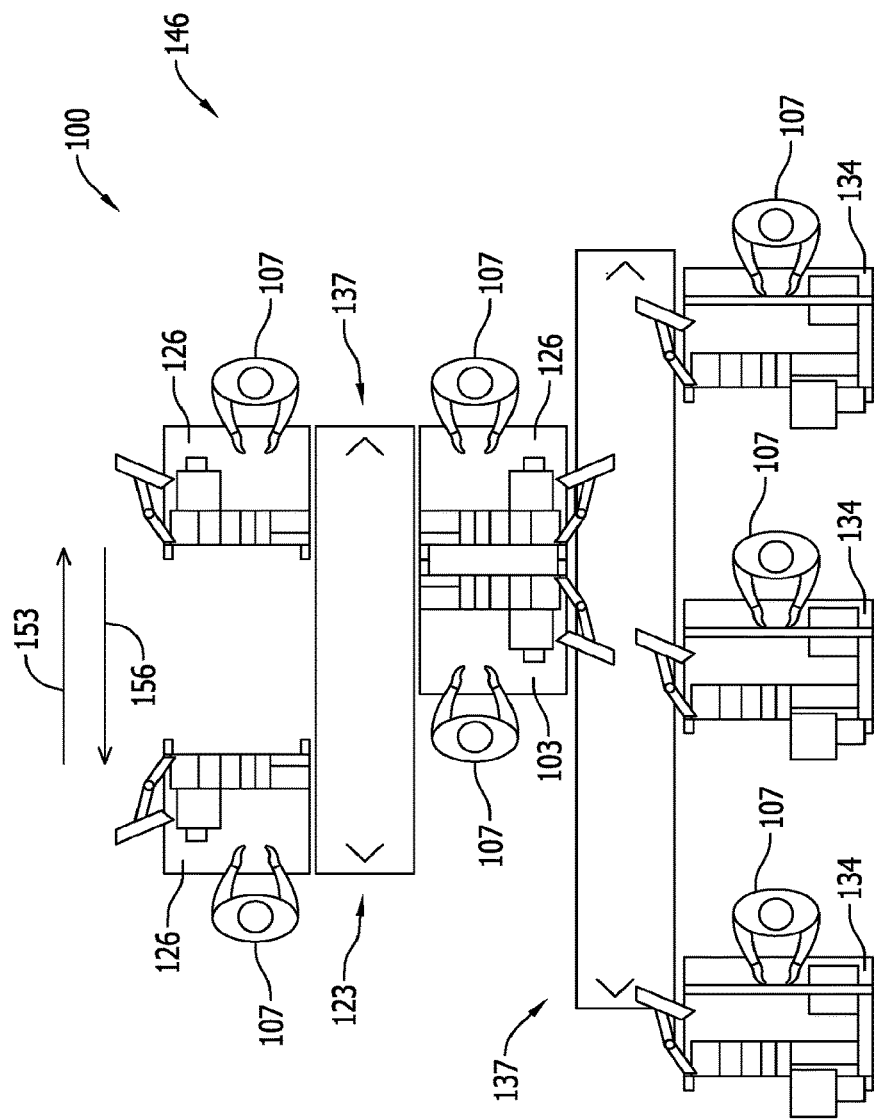
FIG. 3 is a partial plan view of a layout of an ambient condition pharmacy processing system for use with the system shown in FIG. 2 according to an example embodiment.
Figure 4:
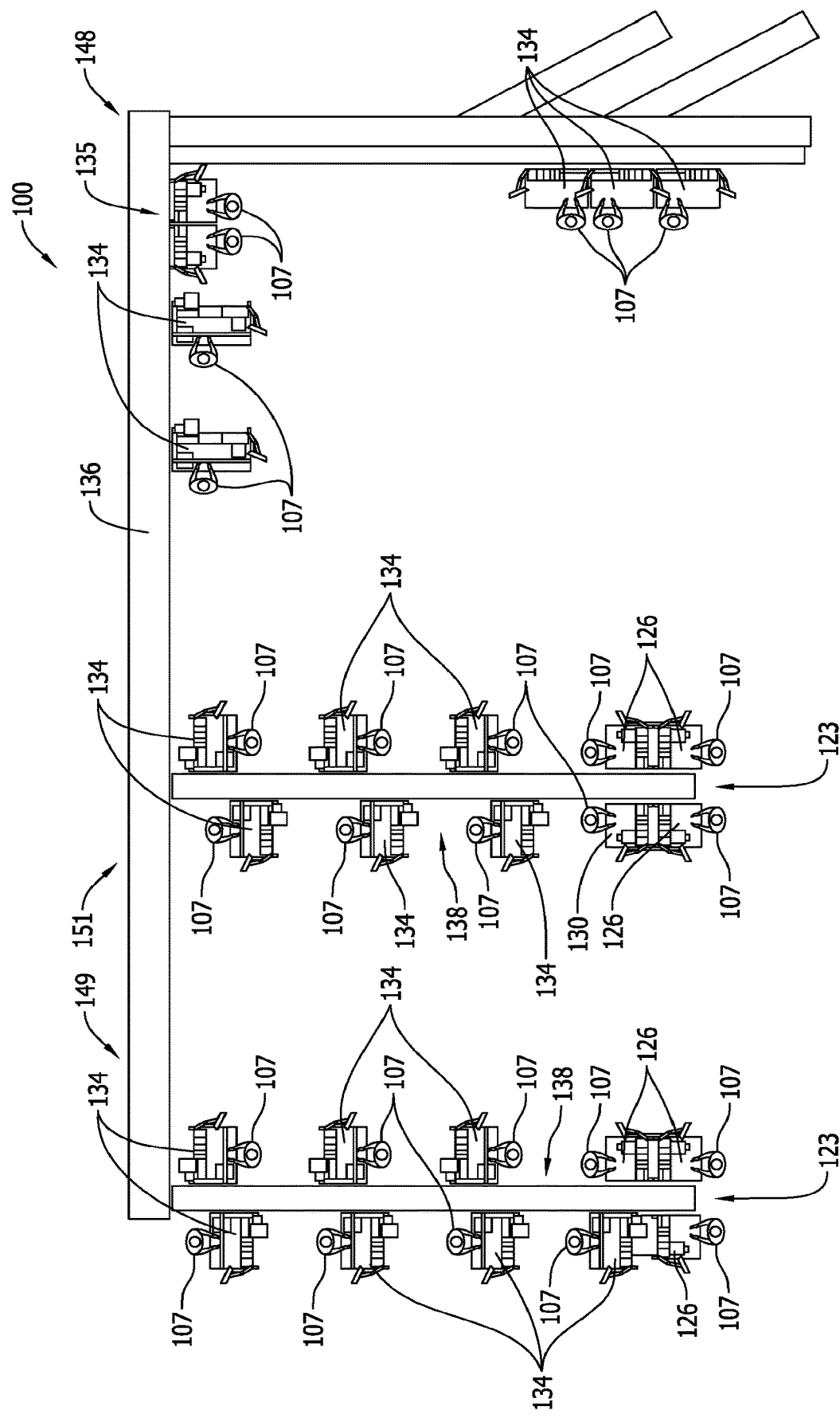
FIG. 4 is a partial plan view of a layout of a refrigerated condition pharmacy processing system for use with the system shown in FIG. 1 according to an example embodiment.

FIGS. 3-4 are partial plan views of specific portions of the prescription order processing system 100 (shown in FIG. 2). More specifically, FIG. 3 is a partial plan view of a layout of the ambient condition section 146 that may be used with the prescription order processing system 100 (shown in FIG. 1). FIG. 4 is a partial plan view of a layout of the refrigerated condition section 148 that may be used with the prescription order processing system 100 (shown in FIG. 2).

In this embodiment, the ambient section 146 includes two full-time ambient picking workstations 126 and one (as-needed) ambient picking workstation 126. The two full-time ambient picking workstations 126 are located on a first side of a first ambient conveyor 137 and the part-time ambient picking workstation 126 is located on a second side of the first ambient conveyor 137, opposite the two full-time ambient picking workstations 126. Each of the ambient conveyors 137 is a single-tier conveyor configured to transport trays 140, filled orders 144, and filled orders in packing boxes 142 within ambient conditions section 146 using gravity. In an additional example, each of the ambient conveyors 137 is powered and is configured to operate in a forward direction 153 and a reverse direction 156. Note that the conveyors may also be gravity fed, rather than powered. A tray drop-off station 123 is positioned adjacent to an end of the first ambient conveyor 137.

An ambient inspection workstation 130 is positioned between the second side of the first ambient conveyor 137 and a first side of a second ambient conveyor 137, adjacent to the part-time ambient picking workstation 126. Three ambient packing workstations 134 are positioned along a second side of the second ambient conveyor 137. Each ambient packing workstation 134 is configured to operate full-time. In this embodiment, each ambient picking workstation 126 is configured to facilitate picking about fifty orders per hour. Each ambient inspection workstation 130 is configured to facilitate inspecting about one hundred eighty orders per hour. Each ambient packing workstation 134 is configured for packing about fifty orders per hour. In some embodiments, each of the workstations 126, 130, and 134 are configured to process any number of orders per hour as enables operation of prescription order processing system 100 as described herein.

In this embodiment, the refrigerated section 148 includes a first refrigerated line 149 and a second refrigerated line 151. The first refrigerated line 149 includes, for example, seven refrigerated packing workstations 134 and, for example, three refrigerated picking workstations 126. The second refrigerated line 151 includes six refrigerated packing workstations 134, three refrigerated picking workstations 126, and one refrigerated inspection workstation 130. Two conveyor assemblies 138 extend between the workstations of each of the first refrigerated line 149 and the second refrigerated line 151 from tray drop-off stations 123 to intersections with the shipping conveyor 136.

Each refrigerated picking workstation 126 is configured to facilitate picking about seventy orders per hour. For example, each refrigerated packing workstation 134 is configured to facilitate packing about thirty orders per hour. The refrigerated inspection workstation 130 is configured to facilitate inspecting, for example, about one hundred eighty orders per hour. With respect to the first refrigerated line 149, for example, four of the refrigerated packing workstations 134 are positioned on a first side of the first conveyor assembly 138 and three of the refrigerated packing workstations 134 are positioned along an opposite second side of the first conveyor assembly. For example, one of the refrigerated picking workstations 126 is positioned along the first side of the first conveyor assembly 138, and two of the refrigerated picking workstations are positioned along the second side of the second conveyor assembly 138. With respect to the second refrigerated line 151, for example, three of the refrigerated packing workstations 134 are positioned along a first side of the second conveyor assembly 138 and three of the refrigerated packing workstations 134 are positioned along an opposite second side of the second conveyor assembly 138. For example, two of the refrigerated picking workstations 126 are positioned along the second side of the second conveyor assembly 138 and one of the refrigerated picking workstations 126 is positioned along the first side of the first conveyor assembly 138. For example, the refrigerated inspection workstation 130 is positioned along the first side of the second conveyor assembly 138 between the refrigerated picking workstation 126 and the refrigerated packing workstations 134.

In this embodiment, for example, the ATX section 147 includes two ATX packing workstations 134 and a pair of quality assurance workstations 135. The shipping conveyor 136 transports filled orders 144, contained within packing containers 142, past the ATX packing workstations 134 and the quality assurance workstations 135 to a plurality of shipping section 150 conveyors that are configured to deliver the filled orders 144 for shipping from the facility. In some embodiments, ATX section 147 may include as many packing workstations 134 and quality assurance workstations 135 as facilitates operation of prescription order processing system 100.

Figure 5:
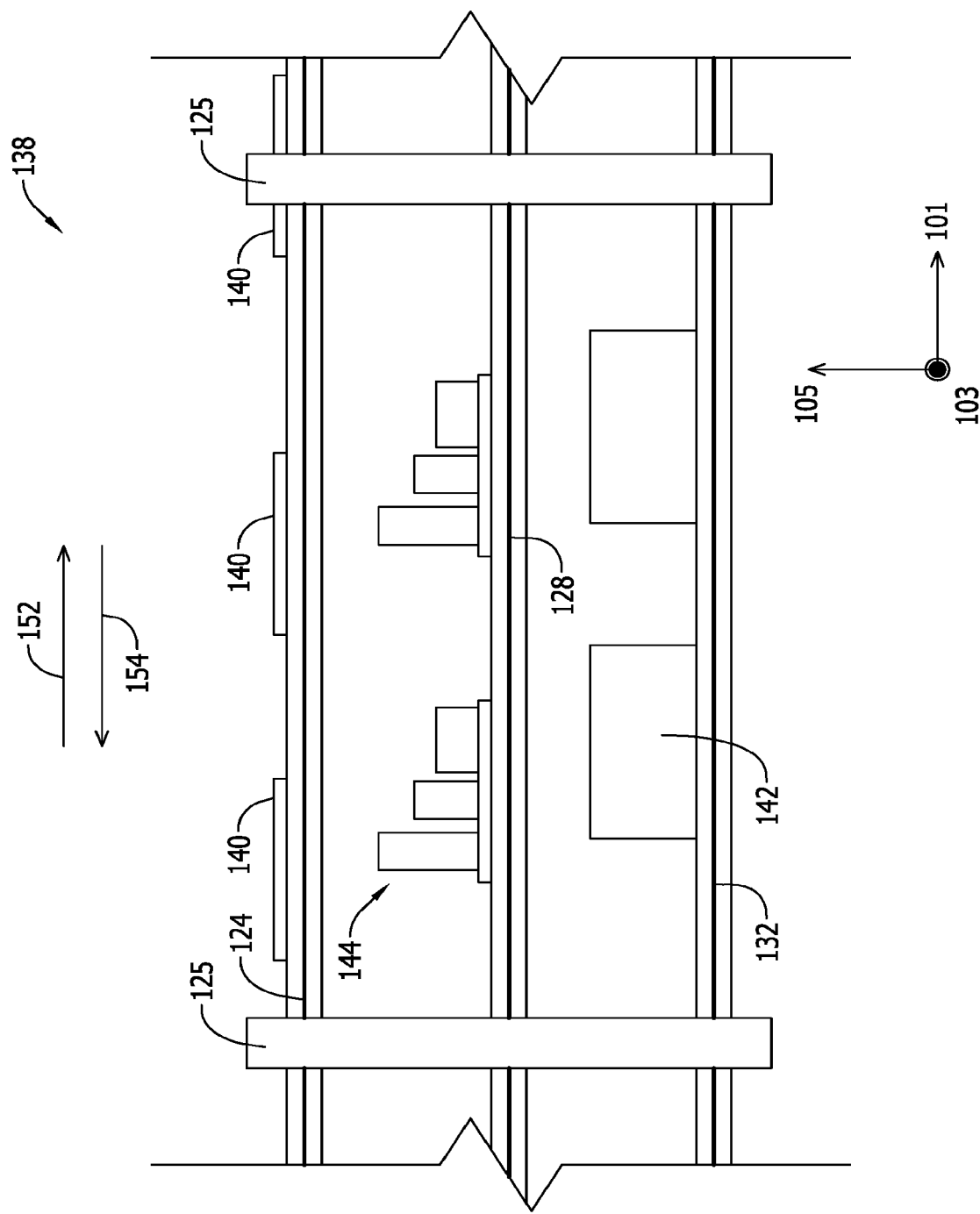
FIG. 5 is a partial side view of a conveyor assembly for use with the refrigerated condition pharmacy processing system shown in FIG. 4 according to an example embodiment.
Figure 6:
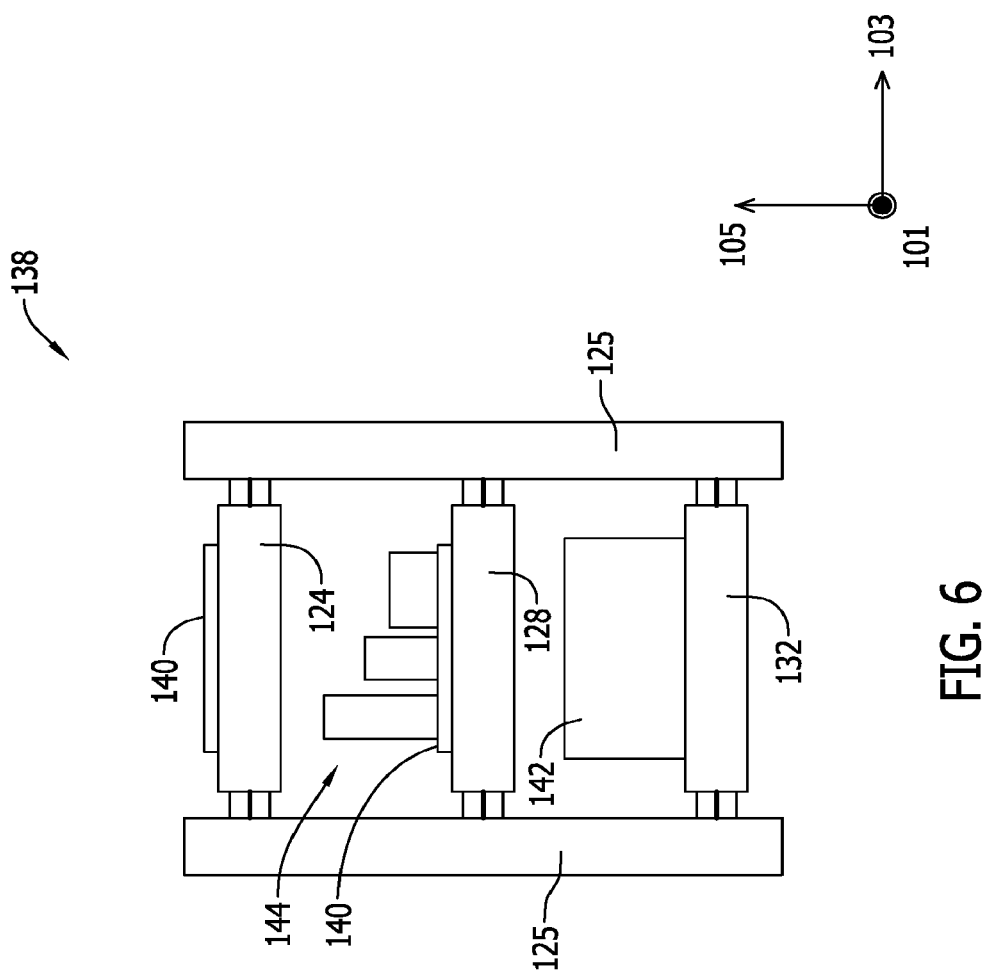
FIG. 6 is a front view of the conveyor assembly shown in FIG. 5 according to an example embodiment.

FIGS. 5-6 are views of the conveyor assembly 138 for use with the refrigerated condition pharmacy processing system 148 (shown in FIG. 4). More specifically, FIG. 5 is a partial side view of the conveyor assembly 138 for use with the refrigerated condition pharmacy processing system 148 (shown in FIG. 4). FIG. 6 is a front view of the conveyor assembly 138 (shown in FIG. 5) according to an example embodiment.

In this embodiment, the conveyor assembly 138 includes a tray delivery conveyor 124 configured to deliver a plurality of trays 140 to the picking workstations 126, a filled order delivery conveyor 128 configured and disposed to deliver a plurality of filled orders 144 to the packing workstations 134 and inspection workstations 130, a packing delivery conveyor 132 configured to deliver the plurality of filled orders 144 packed in packing boxes 142, and a plurality of conveyor supports 125 configured to support conveyor assembly 138. Each of the tray delivery conveyor 124, the filled order delivery conveyor 128, and the packing delivery conveyor 132 of this embodiment is configured to operate in a forward direction 152 and a reverse direction 154. More specifically, each of the tray delivery conveyor 124, the filled order delivery conveyor 128, and the packing delivery conveyor 132 are configured to transport objects (including a tray 140, the packing container 142, and the filled orders 144) along the forward direction 152 and the reverse direction 154. In another embodiment, only some of the tray delivery conveyor 124, the filled order delivery conveyor 128, and the packing delivery conveyor 132 are configured to move in the forward direction 152 and the reverse direction 154.

The tray delivery conveyor 124 of this embodiment extends along a first, longitudinal direction 101. The filled order delivery conveyor 128 extends along the first direction 101 and is spaced apart from the tray delivery conveyor 124 along a second, vertical direction 103, the second direction 103 being substantially orthogonal to the first direction 101. The packing delivery conveyor 132 extends along the first direction 101 and is spaced apart from each of the tray delivery conveyor 124 and the filled order delivery conveyor 128 along the second direction 103. Each of the tray delivery conveyor 124, the filled order delivery conveyor 128, and the packing delivery conveyor 132 are aligned along a third, transverse direction 105 orthogonal to the first direction 101 and the second direction 103. In some embodiments, tray delivery conveyor 124, the filled order delivery conveyor 128, and the packing delivery conveyor 132 extend in differing directions and are spaced apart from each other in any arrangement that facilitates operation of the prescription order processing system 100 as described herein.

The conveyor assembly 138 facilitates efficient use of floor space in facilities where vertical space is available for a tiered conveyor format. By stacking the conveyors in a tiered arrangement such that tray delivery conveyor 124 is positioned above the filled order delivery conveyor 128, which in turn is positioned above the packing delivery conveyor 132, wherein all of the conveyors are aligned along the same direction, workstations having distinct functionality may be positioned in spatially-near relationships. For example, a first operator 107 at a picking workstation 126 may remove a tray 140 from the tray delivery conveyor 124, pick the products from the picking workstation 126 necessary to fulfill a prescription filled order 144, and place the filled order 144 and tray 140 onto the filled order delivery conveyor 128, directly below the tray delivery conveyor 124. In an alternative example, the first operator 107 at the picking workstation 126 may remove the tray 140 from the filled order delivery conveyor 128, pick the products from the picking workstation 126 necessary to fulfill a prescription filled order 144, and place the filled order 144 and tray 140 onto the tray delivery conveyor 124. An operator 107 at an immediately adjacent packing workstation 134 positioned beside the conveyor assembly 138 may then remove the tray 140 containing the filled order 144 and complete the packing process. The operator 107 at the packing workstation 134 may then place the filled order 144 and the packing box 142 containing the filled order 144 onto the lowest, packing delivery conveyor 132 for transit to the shipping section 150 of the prescription order processing system 100.

In the example embodiment, the packing workstations 134 may be ATX packing workstations 134 or any other type of packing workstation that facilitates operation of the prescription order processing system 100 as described herein. In an alternative embodiment, the trays 140, the prescription filled orders 144, and the packing boxes 142 may be directed between the picking workstations 126 and the packing workstations 134 using bottle conveyors, rolling carts, and/or flat belt conveyors, for example. Additionally, enabling the conveyors to operate in the forward direction 152 and reverse direction 154 facilitates rapid and efficient processing of the prescription orders. In further alternative embodiments, the picking workstations 126 and the packing workstations 134 may be coupled in product communication in any manner that facilitates operation of the prescription order processing system 100 as described herein.

Figure 7:
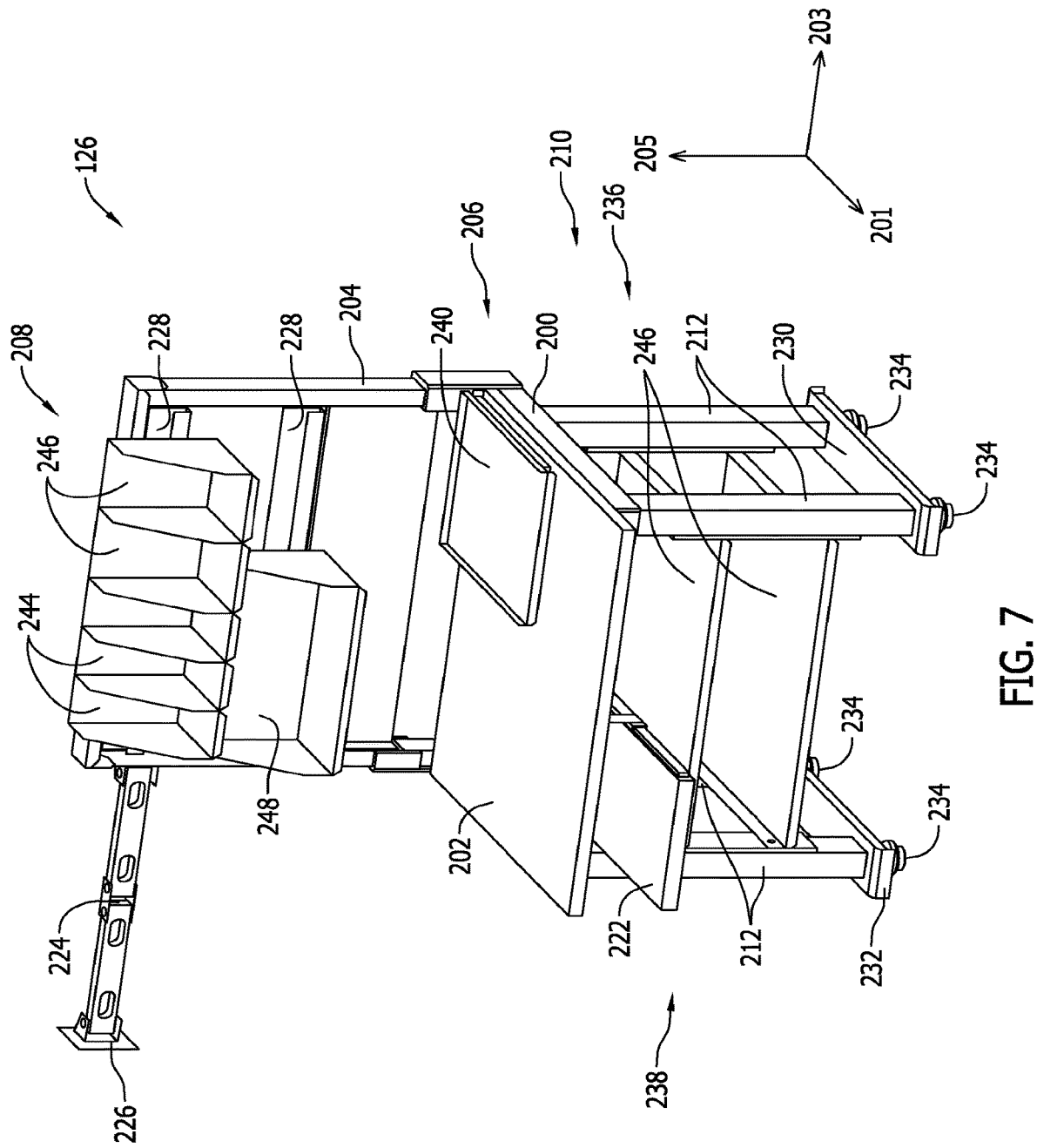
FIG. 7 is a perspective view of a picking workstation for use with the system shown in FIG. 1 according to an example embodiment.
Figure 8:
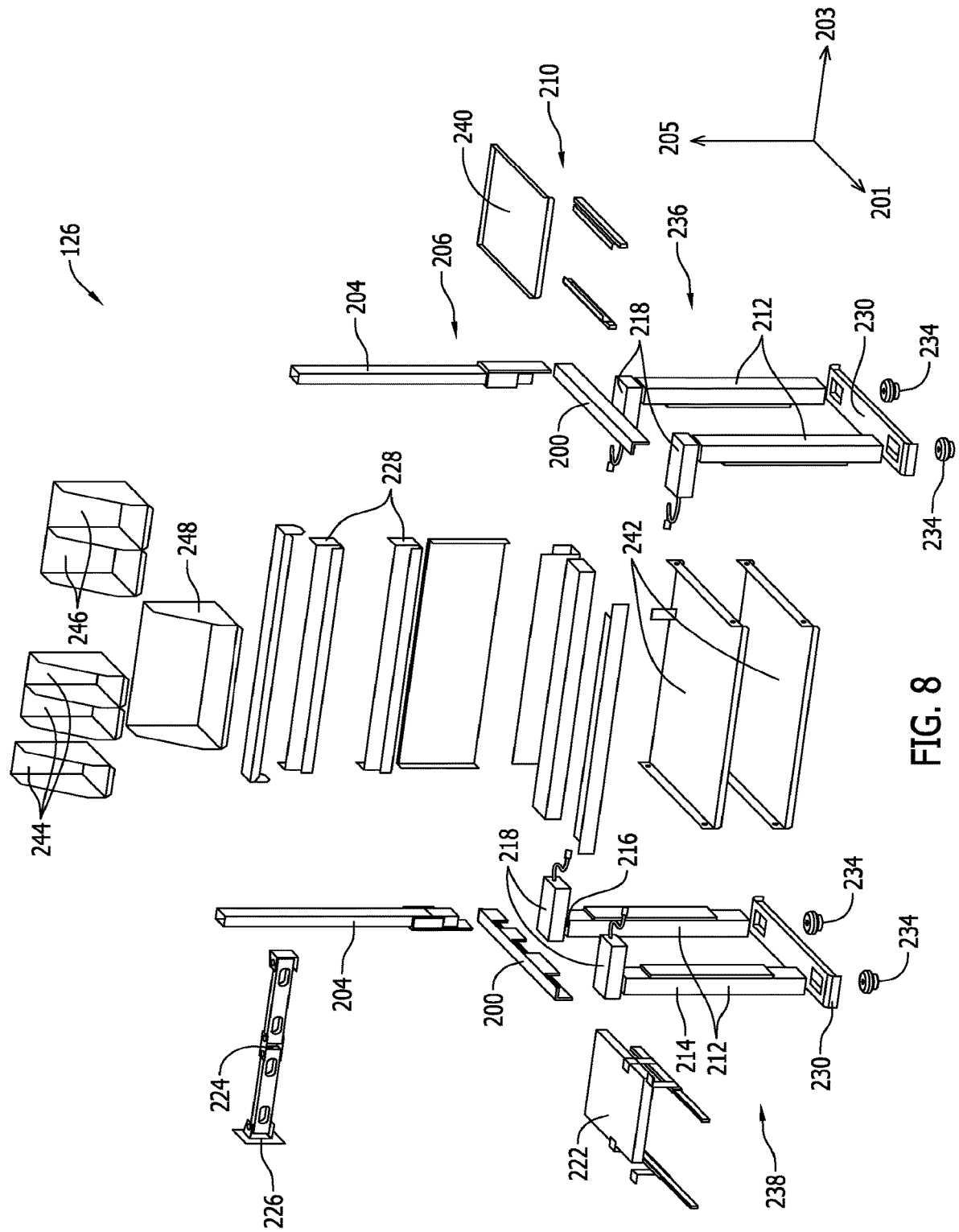
FIG. 8 is an exploded perspective view of the picking workstation shown in FIG. 7 according to an example embodiment.

FIGS. 7-8 are views of the picking workstation 126 for use with the prescription order processing system 100 (shown in FIG. 2). More specifically, FIG. 7 is a perspective view of a picking workstation 126 for use with the prescription order processing system 100. FIG. 8 is an exploded perspective view of the inspection workstation 130 (shown in FIG. 7).

In this embodiment, picking workstation 126 includes a support frame 200, a desktop 202 connected to the support frame 200, an accessory frame 204 connected to a rear portion 206 of the support frame 200, and a base 210 connected to the support frame 200. The support frame 200 extends along a first, longitudinal direction 201 and a second, transverse direction 203, the second direction 203 perpendicular to the first direction 201. The accessory frame 204 extends along a third, vertical direction 205, the third direction 205 being orthogonal to the first direction 201 and the second direction 203. The base 210 extends oppositely from the accessory frame 204 along the second direction 203 and includes a pair of storage shelfs 242.

A support tray 222 of this embodiment is connected to a bottom face 220 of the desktop 202 and extends along the first direction 201. An arm 224 is connected to the accessory frame 204 and is configured to rotate in a plane orthogonal to the third direction 205. The arm 224 includes an accessory mounting block 226 that is configured to facilitate mounting of accessories including, but not limited to, computer monitors, displays, and reference charts. A plurality of support beams 228 are connected to the accessory frame 204 and extend along the second direction, each of the support beams 228 configured to retain a plurality of storage bins 208. The storage bins 208 are connected to the support beams 228 and include three first storage bins 244, two second storage bins 246, and one third storage bin 248. Each of the storage bins 244, 246, and 248 are configured to store products of certain sizes corresponding to the storage bin size for retrieval as part of completing a filled order 144. In the example embodiment, each of first storage bins 244 has a first volume, each of second storage bins 246 has a second volume being larger than the first volume, and each of third storage bins 248 has a third volume being larger than the second volume. In one embodiment, first storage bins 244 are configured to retain dispensing bottles, second storage bins 246 are configured to retain auxiliary labels, and third storage bins 248 are configured to retain bags. In other alternative embodiments, any of storage bins 244, 246, and 248 may be of any size and may be configured to retain dispensing bottles, auxiliary labels, bags, envelopes, and tape dispensers. In some embodiments, picking workstation 126 may include as many types of accessories connected to picking workstation 126 as facilitates operation of prescription order processing system 100 as described herein.

The base 210 includes four legs 212, a first foot 230, and a second foot 232. The first foot 230 is connected to a first pair 236 of legs 212 and the second foot 232 is connected to a second pair 238 of legs 212. Each of the first foot 230 and the second foot 232 extends along the first direction 201 and is positioned opposite the other foot along the second direction 203. A pair of leveling feet 234 are connected to each of the first foot 230 and the second foot 232, and are configured to be adjusted to raise and/or lower the picking workstation along the third direction 205 to facilitate leveling of the picking workstation 126.

Each leg 212 includes an outer sleeve 214, an inner support 216, and an extension motor 218. The inner support 216 is positioned within the outer sleeve 214. The extension motor 218 is positioned within each leg 212 and is configured to cause the inner support 216 to extend relative to the outer sleeve 214. The extension motors 218 within each of the four legs 212 may cause the inner support 216 to extend to a plurality of positions relative to the outer sleeve 214 and permit the positioning of the desktop 202 in an anatomically correct position for a prescription order processing system employee. In an alternative example, each leg 212 may include only outer sleeve 214 and may be fixed. For example, the position of desktop 202 relative to the prescription order processing system employee may be non-adjustable.

Figure 9:
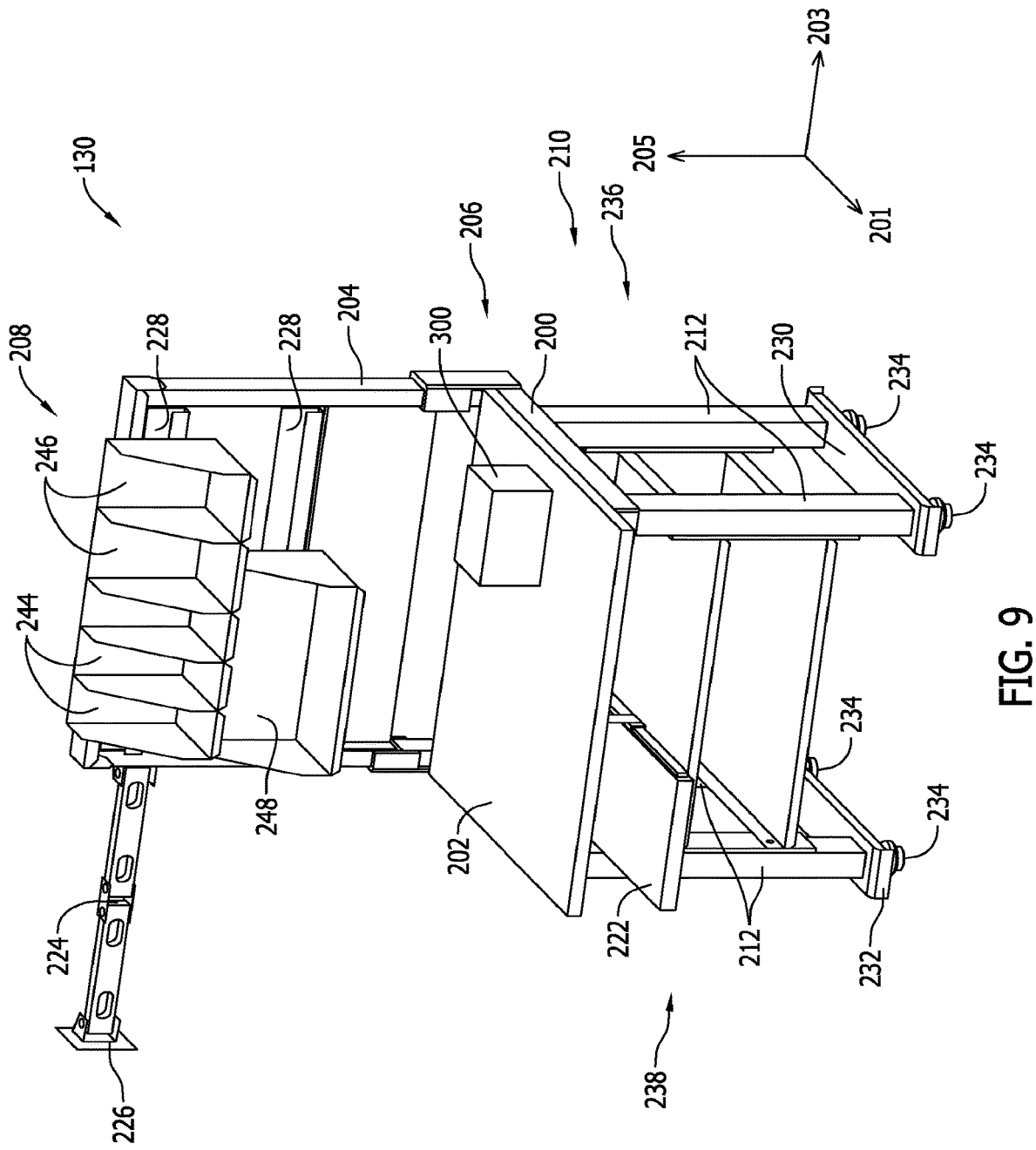
FIG. 9 is a perspective view of an inspection workstation for use with the system shown in FIG. 1 according to an example embodiment.

FIG. 9 is a perspective view of an inspection workstation 130 for use with the prescription order processing system 100 (shown in FIG. 2) according to the example embodiment. The embodiment shown in FIG. 9 is substantially identical to the embodiment of the picking workstation 126 shown in FIGS. 7-8, except desktop 202 does not include a shelf 240 and the inspection workstation 130 includes a product scanner 300. Product scanner 300 is configured to scan the contents of the filled orders 144 to verify that the correct products have been compiled to the filled orders 144.

Figure 10:
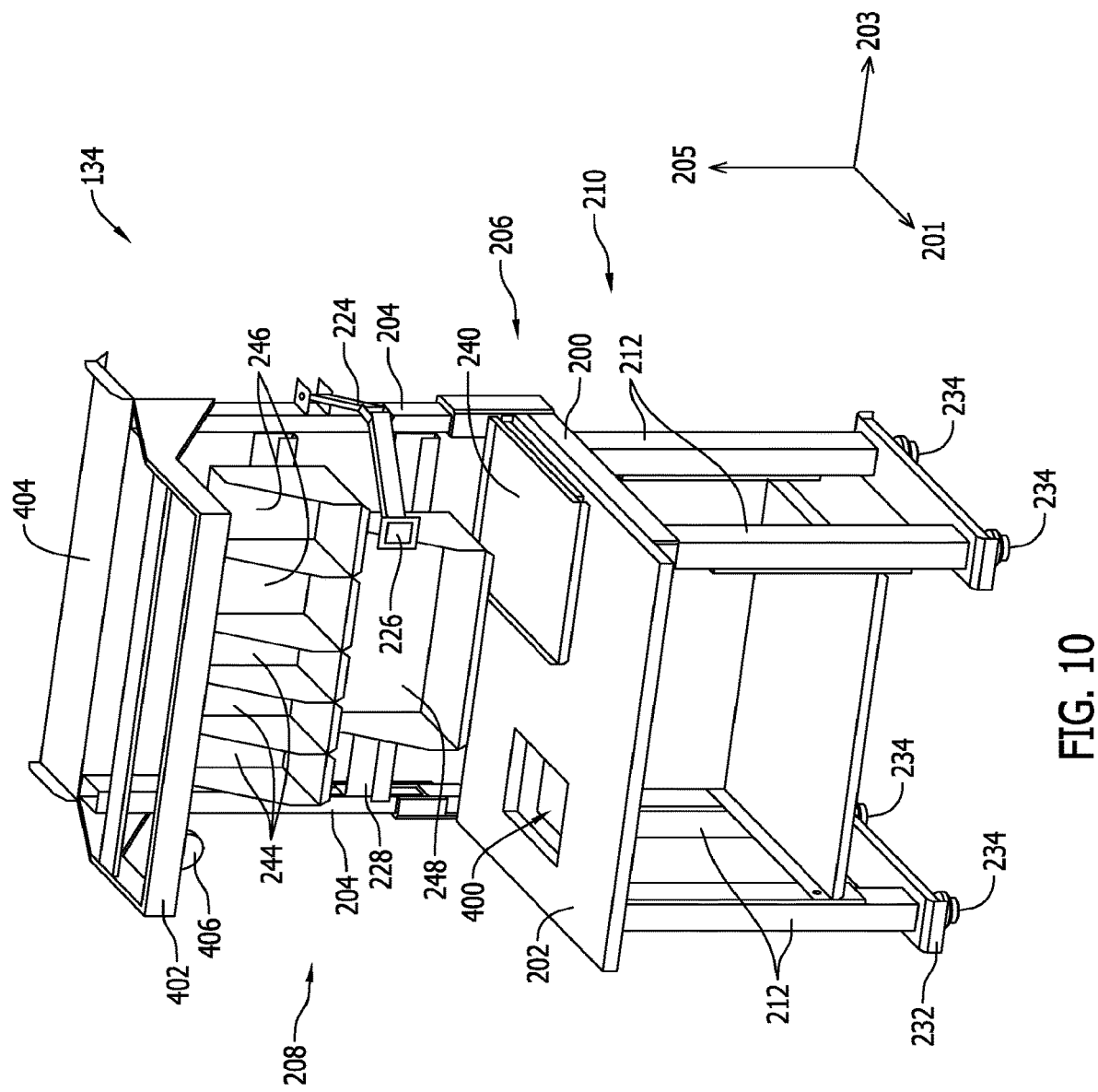
FIG. 10 is a perspective view of a packing workstation for use with the system shown in FIG. 1 according to an example embodiment.

FIG. 10 is a perspective view of a packing workstation 134 for use with the prescription order processing system 100 (shown in FIG. 2) according to the example embodiment. The embodiment shown in FIG. 10 is substantially identical to the embodiment of the picking workstation 126 shown in FIGS. 7-8, except the packing workstation 134 does not include a support tray 222 but does include an overhead frame 402, an overhead brace 404, and a tool trolley 406. Additionally, the desktop 202 defines a scale opening 400 that is configured to receive a scale to facilitate weighing of the filled orders 144. In some embodiments, the packing workstation 134 may include a plurality of receptacles that are configured to receive shipping label printers. In yet another embodiment, packing workstation 134 may more than one tool trolley 406.

In this embodiment, the overhead frame 402 is connected to the accessory frame 204 and extends in the first direction 201. The overhead brace 404 is connected to the accessory frame 204 and extends oppositely from the overhead frame 402 along the first direction. The tool trolley 406 is moveably connected to the overhead frame 402 and is configured to i) support a load and ii) move along the second direction. In some embodiments, tool trolley 406 may support attachments configured to facilitate moving filled orders from ambient conveyor 137 and/or conveyor assembly 138 to a scale within scale opening 400. In other embodiments, packing workstation 134 may include as many tool trolleys as facilitates operation of packing workstation 134.

Figure 11:
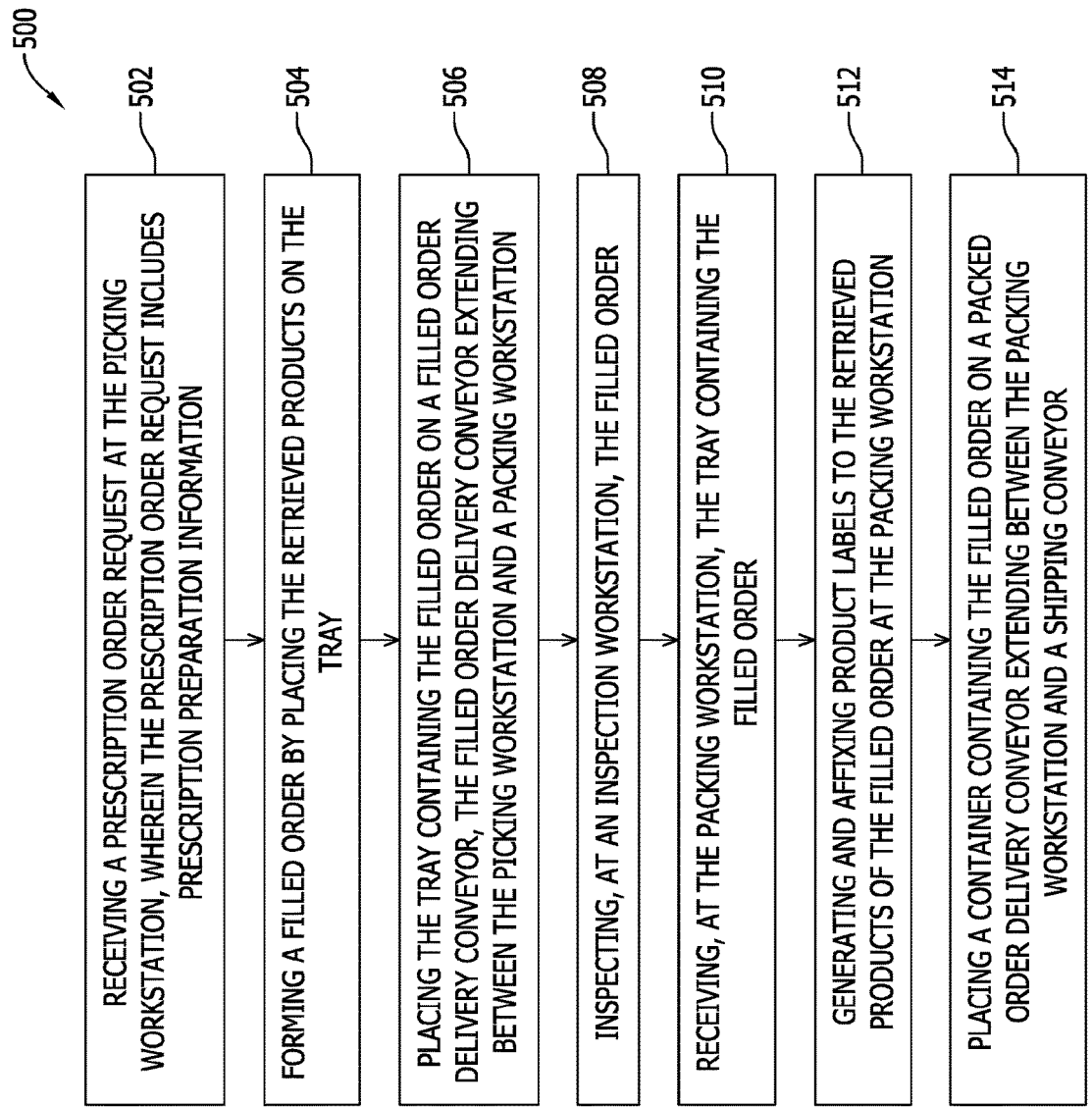
FIG. 11 is an example process flow illustrating a method for processing pharmacy orders, according to an example embodiment.

FIG. 11 is an example process flow illustrating a method 500 for processing pharmacy orders, according to one embodiment. Method 500 includes receiving 502, by an operator 107, a prescription order request at a picking workstation 126, wherein the prescription order request includes prescription preparation information. Method 500 also includes forming 504, by an operator 107, a filled order 144 by placing a plurality of retrieved products on a tray 140. Method 500 further includes placing 506, by an operator 107, the tray 140 containing the filled order 144 on a filled order delivery conveyor 128, the filled order delivery conveyor 128 extending between the picking workstation 126 and a packing workstation 134. In other embodiments, method 500 may include additional steps to facilitate retrieving products and forming a filled order as part of the pharmacy order processing process.

Method 500 also includes inspecting 508, at an inspection workstation 130, by an operator 107, the filled order 144. Method 500 also includes receiving 510, at the packing workstation 134, by an operator 107, the tray 140 containing the filled order 144. Method 500 further includes generating and affixing 512, by an operator 107, product labels to the retrieved products of the filled order 144 at the packing workstation 134. Finally, method 500 includes placing 514, by an operator 107, a packing container 142 containing the filled order 144 on a packing delivery conveyor 132 extending between the packing workstation 134 and a shipping conveyor 136. In other embodiments, method 500 may include additional workstations or conveyors to process the filled order 144.

Embodiments of the methods and systems described herein achieve superior results as compared to prior methods and systems. For example, unlike known pharmacy order processing systems, the pharmacy order processing systems described are configured to operate in numerous different types of specialty pharmacies. In particular, the picking workstations, the packing workstations, the inspection workstations, and the conveyor assemblies described are configurable between a plurality of specialty pharmacy order processing system layouts such that the components of the system may be installed and operated in a variety of different applications without regard to a specific ordering or configuration of the components. As a result, specialty and custom pharmacies can be retrofitted with workstations and conveyor assemblies having custom-configurable and modern features, thereby increasing the efficiency of existing specialty pharmacies. These workstations can also have bottle conveyors incorporated next to them, along with rolling carts that can be used to process the orders. Flat belt conveyors can also be used in conjunction with these stations and their functionality. Further, unlike some known pharmacy order processing workstations that have fixed configurations, the workstations described herein allow a pharmacy and/or an operator to select and configure numerous different user-configurable options such as product container size and position and the positioning of the workstation relative to the operator. Additionally, unlike some known pharmacy order processing conveyor assemblies, the conveyor assemblies described herein include multi-directional tiered conveyors that can transport filled orders between the workstations while efficiently utilizing available floor space and allowing workstations of differing functionality to be co-located in a given area.

The term "based on" or using, as used herein, reflects an open-ended term that can reflect others elements beyond those explicitly recited. Certain systems, apparatus, applications or processes are described herein as including a number of modules. A module may be a unit of distinct functionality that may be presented in software, hardware, or combinations thereof. When the functionality of a module is performed in any part through software, the module includes a computer-readable medium. The modules may be regarded as being communicatively coupled.

The embodiments of the present disclosure generally provide for a plurality of circuits or other electrical devices, which can be used in units, modules, systems, and subsystems and the like. All references to such and the functionality provided by each are not intended to be limited to encompassing only what is illustrated and described herein. While particular labels may be assigned to the various circuits or other electrical devices disclosed, such labels are not intended to limit the scope of operation for the circuits and the other electrical devices. Such circuits and other electrical devices may be combined with each other and/or separated in any manner based on the particular type of electrical/operational implementation that is desired. It is recognized that any circuit or other electrical device disclosed herein may include any number of microprocessors, discrete circuit components, integrated circuits, memory devices (e.g., FLASH, random access memory (RAM), read only memory (ROM), electrically programmable read only memory (EPROM), electrically erasable programmable read only memory (EEPROM), or other suitable variants thereof, etc.) and instructions (e.g., software, etc.) which co-act with one another to perform operation(s) disclosed herein. In addition, any one or more than one electric devices may be configured to execute a computer-program that is embodied in a computer readable medium that is programmed to perform any number of the functions and features as disclosed. The computer readable medium may be non-transitory or in any form readable by a machine or electrical component.

At least some portions of the present disclosure may be accomplished by using a robot. A robot can be a machine capable of carrying out a complex series of actions automatically. These complex series of actions may include picking up, orientating, positioning and/or releasing a prescription component, a pill, a container or other structure. The robot may be dedicated to a single series of movements or may be able to execute multiple series of movements. A robot may include a processor that received instructions and then executes instructions to control its movement. In another example, a robot may resemble a human being and replicate certain human movements and functions, may move location, have an articulated arm, have grasping structures that replicate fingers and do not damage containers, and the like.

Methods and systems for pharmacy order processing have been described. Although embodiments of the present disclosure have been described with reference to specific example embodiments, it will be evident that various modifications and changes may be made to these embodiments without departing from the broader spirit and scope of the embodiments of the disclosure. Accordingly, the specification and drawings are to be regarded in an illustrative rather than a restrictive sense.

The methods described herein do not have to be executed in the order described, or in any particular order. Moreover, various activities described with respect to the methods identified herein can be executed in serial or parallel fashion. Although "End" blocks may be shown in the flowcharts, the methods may be performed continuously.

In the foregoing, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus, the following claims are hereby incorporated into the Detailed Description, with each claim standing on its own as a separate embodiment.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims It should be understood that one or more than one steps within a method may be executed in different order (or concurrently) without altering the principles of the present disclosure. Further, although each of the embodiments is described above as having certain features, any one or more than one of those features described with respect to any embodiment of the disclosure can be implemented in and/or combined with features of any of the other embodiments, even if that combination is not explicitly described. In other words, the described embodiments are not mutually exclusive, and permutations of one or more than one embodiments with one another remain within the scope of this disclosure.

Spatial and functional relationships between elements (for example, between modules, circuit elements, semiconductor layers, etc.) are described using various terms, including "connected," "engaged," "coupled," "adjacent," "next to," "on top of," "above," "below," and "disposed." Unless explicitly described as being "direct," when a relationship between first and second elements is described in the above disclosure, that relationship can be a direct relationship where no other intervening elements are present between the first and second elements, but can also be an indirect relationship where one or more than one intervening elements are present (either spatially or functionally) between the first and second elements. As used herein, the phrase at least one of A, B, and C should be construed to mean a logical (A ORB OR C), using a non-exclusive logical OR, and should not be construed to mean "at least one of A, at least one of B, and at least one of C."

In this application, including the definitions below, the term 'module' or the term 'controller' may be replaced with the term 'circuit.' The term 'module' may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The module may include one or more than one interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

The term code, as used above, may include software, firmware, and/or microcode, and may refer to programs, routines, functions, classes, data structures, and/or objects. The term shared processor circuit encompasses a single processor circuit that executes some or all code from multiple modules. The term group processor circuit encompasses a processor circuitry that, in combination with additional processor circuits, executes some or all code from one or more than one modules. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple modules. The term group memory circuit encompasses a memory circuit that, in combination with additional memories, stores some or all code from one or more than one modules.

The term memory circuit is a subset of the term computer-readable medium. The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory, tangible computer-readable medium are nonvolatile memory circuits (such as a flash memory circuit, an erasable programmable read-only memory circuit, or a mask read-only memory circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The systems and methods described in this application may be partially or fully implemented by a special purpose computer created by configuring a general purpose computer to execute one or more than one particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory, tangible computer-readable medium. The computer programs may also include or rely on stored data. The computer programs may encompass a basic input/output system (BIOS) that interacts with hardware of the special purpose computer, device drivers that interact with particular devices of the special purpose computer, one or more than one operating systems, user applications, background services, background applications, etc.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Swift, Haskell, Go, SQL, R, Lisp, Java®, Fortran, Perl, Pascal, Curl, OCaml, Javascript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

None of the elements recited in the claims are intended to be a means-plus-function element within the meaning of 35 U.S.C. § 112(f) unless an element is expressly recited using the phrase "means for," or in the case of a method claim using the phrases "operation for" or "step for."

Embodiments for pharmacy order processing are described above in detail. The systems and methods of operating such systems are not limited to the specific embodiments described herein, but rather, components of systems and/or steps of the methods may be utilized independently and separately from other components and/or steps described herein. For example, the methods may also be used in combination with other systems and environments and are not limited to the environments as described herein. Rather, the embodiments can be implemented and utilized in connection with many other applications.

In this specification and the claims, reference is made to a number of terms, which shall be defined to have the following meanings:

The singular forms "a", "an", and "the" include plural references unless the context clearly dictates otherwise.

"Optional" or "optionally" means that the subsequently described event or circumstance may or may not occur, and that the description includes instances where the event occurs and instances where it does not.

The term "non-transitory computer-readable media" is intended to be representative of any tangible computer-based device implemented in any method or technology for short-term and long-term storage of information, such as, computer-readable instructions, data structures, program modules and sub-modules, or other data in any device. Therefore, the methods described herein may be encoded as executable instructions embodied in a tangible, non-transitory, computer readable medium, including, without limitation, a storage device and/or a memory device. Such instructions, when executed by a processor, cause the processor to perform at least a portion of the methods described herein. Moreover, as used herein, the term "non-transitory computer-readable media" includes all tangible, computer-readable media, including, without limitation, non-transitory computer storage devices, including, without limitation, volatile and nonvolatile media, and removable and non-removable media such as a firmware, physical and virtual storage, cd-roms, dvds, and any other digital source such as a network or the internet, as well as yet to be developed digital means, with the sole exception being a transitory, propagating signal.

The terms "software" and "firmware" are interchangeable, and include any computer program stored in memory for execution by devices that include, without limitation, mobile devices, clusters, personal computers, workstations, clients, and servers.

The term "computer" and related terms, e.g., "computing device", are not limited to integrated circuits referred to in the art as a computer, but broadly refers to a microcontroller, a microcomputer, a programmable logic controller (plc), an application specific integrated circuit, and other programmable circuits, and these terms are used interchangeably herein.

Computer systems are described, and such computer systems include a processor and a memory. However, any processor in a computer device referred to may also refer to one or more processors wherein the processor may be in one computing device or a plurality of computing devices acting in parallel, such as in a cloud computing environment. Additionally, any memory in a computer device referred to may also refer to one or more memories, wherein the memories may be in one computing device or a plurality of computing devices acting in parallel.

A processor may include any programmable system including systems using micro-controllers, reduced instruction set circuits (rise), application specific integrated circuits (asics), logic circuits, and any other circuit or processor capable of executing the functions described herein. The above examples are example only, and are thus not intended to limit in any way the definition and/or meaning of the term "processor." The term "database" may refer to either a body of data, a relational database management system (rdbms), or to both. A database may include any collection of data including hierarchical databases, relational databases, flat file databases, object-relational databases, object oriented databases, and any other structured collection of records or data that is stored in a computer system. The above are only examples, and thus are not intended to limit in any way the definition and/or meaning of the term database. Examples of rdbms's include, but are not limited to including, Oracle® Database, Mysql, IBM® Db2, Microsoft® Sql Server, Sybase®, and Postgresql. However, any database may be used that enables the systems and methods described herein. (oracle is a registered trademark of Oracle Corporation, Redwood Shores, Calif.; IBM is a registered trademark of International Business Machines Corporation, Armonk, N.Y.; Microsoft is a registered trademark of Microsoft Corporation, Redmond, Wash.; and Sybase is a registered trademark of Sybase, Dublin, Calif.)

In some embodiments, a computer program is embodied on a computer readable medium. In other embodiments, the system is executed on a single computer system, without requiring a connection to a server computer. In still other embodiments, the system is run in a windows® environment (windows is a registered trademark of Microsoft corporation, Redmond, Wash.). In yet another embodiment, the system is run on a mainframe environment and a Unix® server environment (Unix is a registered trademark of x/open company limited located in reading, Berkshire, United Kingdom). The application is flexible and designed to run in various different environments without compromising any major functionality. In some embodiments, the system includes multiple components distributed among a plurality of computing devices. One or more components may be in the form of computer-executable instructions embodied in a computer-readable medium.

Approximating language, as used herein throughout the specification and claims, may be applied to modify any quantitative representation that could permissibly vary without resulting in a change in the basic function to which it is related. Accordingly, a value modified by a term or terms, such as "about" and "substantially", are not to be limited to the precise value specified. In at least some instances, the approximating language may correspond to the precision of an instrument for measuring the value. Here and throughout the specification and claims, range limitations may be combined and/or interchanged; such ranges are identified and include all the sub-ranges contained therein unless context or language indicates otherwise.

The inventive subject matter may be represented in a variety of different embodiments of which there are many possible permutations. Although specific features of various embodiments of the invention may be shown in some drawings and not in others, this is for convenience only. In accordance with the principles of the invention, any feature of a drawing may be referenced and/or claimed in combination with any feature of any other drawing. This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

We claim:

1. A workstation for a pharmacy order processing system, the workstation comprising:
a support frame;
a desktop connected to the support frame;
an accessory frame connected to a rear portion of the support frame;
a plurality of storage bins moveably connected to the accessory frame, the storage bins extending toward the desktop and being open toward the desktop; and
the support frame including:
a base including:
four legs, each leg including:
an outer sleeve;
an inner support positioned within the outer sleeve; and
an extension motor positioned within each leg and configured to extend the inner support relative to the outer sleeve to adjust a height of desktop.

2. The workstation of claim 1, wherein the support frame extends along a first direction and a second direction, the second direction perpendicular to the first direction.

3. The workstation of claim 2, wherein a support tray is connected to a bottom face of the desktop and is configured to be extendable along the first direction.

4. The workstation of claim 2, wherein the accessory frame extends along a third direction orthogonal to the first direction and the second direction.

5. The workstation of claim 4, wherein the accessory frame includes:
an arm connected to the accessory frame and configured to rotate a in a plane orthogonal to the third direction, the arm including an accessory mounting block; and
a plurality of support beams extending along the second direction, each of the support beams configured to retain a plurality of storage bins.

6. The workstation of claim 4, wherein the base extends oppositely from the accessory frame along the second direction.

7. The workstation of claim 6, wherein the base further includes a first foot and a second foot, wherein the first foot is connected to a first pair of legs and the second foot is connected to a second pair of legs, and wherein each foot extends along the first direction and is positioned opposite the other foot along the second direction.

8. The workstation of claim 1, wherein the desktop further defines an opening configured to receive a scale.

9. The workstation of claim 2 further including an overhead frame connected to the accessory frame, the overhead frame extending in the first direction.

10. The workstation of claim 9, wherein the overhead frame includes a tool trolley configured to support a load and move along the second direction.

11. A workstation for a pharmacy order processing system, the workstation comprising:
- a support frame;
- a desktop connected to the support frame;
- an accessory frame connected to a rear portion of the support frame,
- the support frame including:
  - storage bins connected to the accessory frame to store various sizes of pharmacy products, respectively; and
  - a base connected to the support frame, the base including:
    - four legs, each leg including:
      - an outer sleeve;
      - an inner support moveably positioned within the outer sleeve; and
      - an extension motor positioned within each leg and configured to extend the inner support relative to the outer sleeve to adjust the height of the desktop relative to a height of a conveyor adjacent the desktop.

12. The workstation of claim 11, wherein the support frame extends along a first direction and a second direction, the second direction perpendicular to the first direction.

13. The workstation of claim 12, wherein a support tray is connected to a bottom face of the desktop and is configured to be extendable along the first direction.

14. The workstation of claim 12, wherein the accessory frame extends along a third direction orthogonal to the first direction and the second direction.

15. The workstation of claim 14, wherein the accessory frame includes:
- an arm connected to the accessory frame and configured to rotate in a plane orthogonal to the third direction, the arm including an accessory mounting block; and
- a plurality of support beams extending along the second direction, each of the support beams configured to retain a plurality of storage bins.

16. The workstation of claim 11, wherein the conveyor is at least one of a tray delivery conveyor, a filled order delivery conveyor, a packing delivery conveyor or a combination thereof and the conveyor is configured to operate in a forward and a reverse direction.

17. The workstation of claim 11, wherein the storage bins include a first storage bin having a first volume, a second storage bin having a second volume larger than the first volume, and a third storage bin having a third volume larger than the second volume.

* * * * *